(12) United States Patent
Omohundro et al.

(10) Patent No.: US 11,076,868 B2
(45) Date of Patent: Aug. 3, 2021

(54) VACUUM DRILL GUIDE

(71) Applicants: Thomas Ward Omohundro, Minden, NV (US); Charles Peter Darby, Minden, NV (US)

(72) Inventors: Thomas Ward Omohundro, Minden, NV (US); Charles Peter Darby, Minden, NV (US)

(73) Assignee: Thomas Ward Omohundro, Minden, NV (US)

( * ) Notice: Subject to any disclaimer, the term of this patent is extended or adjusted under 35 U.S.C. 154(b) by 182 days.

(21) Appl. No.: 16/525,507

(22) Filed: Jul. 29, 2019

(65) Prior Publication Data
US 2021/0030430 A1  Feb. 4, 2021

(51) Int. Cl.
*A61B 17/00* (2006.01)
*A61B 17/16* (2006.01)
*A61B 17/17* (2006.01)
*A61M 1/00* (2006.01)

(52) U.S. Cl.
CPC .......... *A61B 17/1633* (2013.01); *A61B 17/17* (2013.01); *A61B 2017/00477* (2013.01); *A61B 2217/005* (2013.01); *A61M 1/0056* (2013.01)

(58) Field of Classification Search
CPC combination set(s) only.
See application file for complete search history.

(56) References Cited

U.S. PATENT DOCUMENTS

| 6,071,284 A | 6/2000 | Fox |
| 2004/0191897 A1* | 9/2004 | Muschler ........... A61B 10/0233 435/325 |

FOREIGN PATENT DOCUMENTS

EP    1849418 A1    10/2007

OTHER PUBLICATIONS

EP20184878, European Search Report, dated Jan. 12, 2020.

* cited by examiner

*Primary Examiner* — Sameh R Boles
(74) *Attorney, Agent, or Firm* — Glass and Associates; Kenneth D'Alessandro; Kenneth Glass

(57) ABSTRACT

A vacuum drill guide includes an elongated structure having an internal axial passageway formed therethrough, a first end of the elongated structure terminating in a drill bushing affixed to a first end of the elongated structure, the drill bushing having an axial slot communicating with the internal axial passageway of the elongated structure, the drill bushing further having a longitudinal bore formed therethrough to receive a drill bit and allow the received drill bit to rotate, a second end of the elongated structure opposite the first end terminating in a vacuum hose fitting communicating with the axial passageway, a chip recovery chamber disposed along the internal axial passageway between the first end and the second end of the elongated structure, and a vacuum filter disposed in the internal axial passageway between the chip recovery chamber and the first end of the elongated structure.

18 Claims, 4 Drawing Sheets

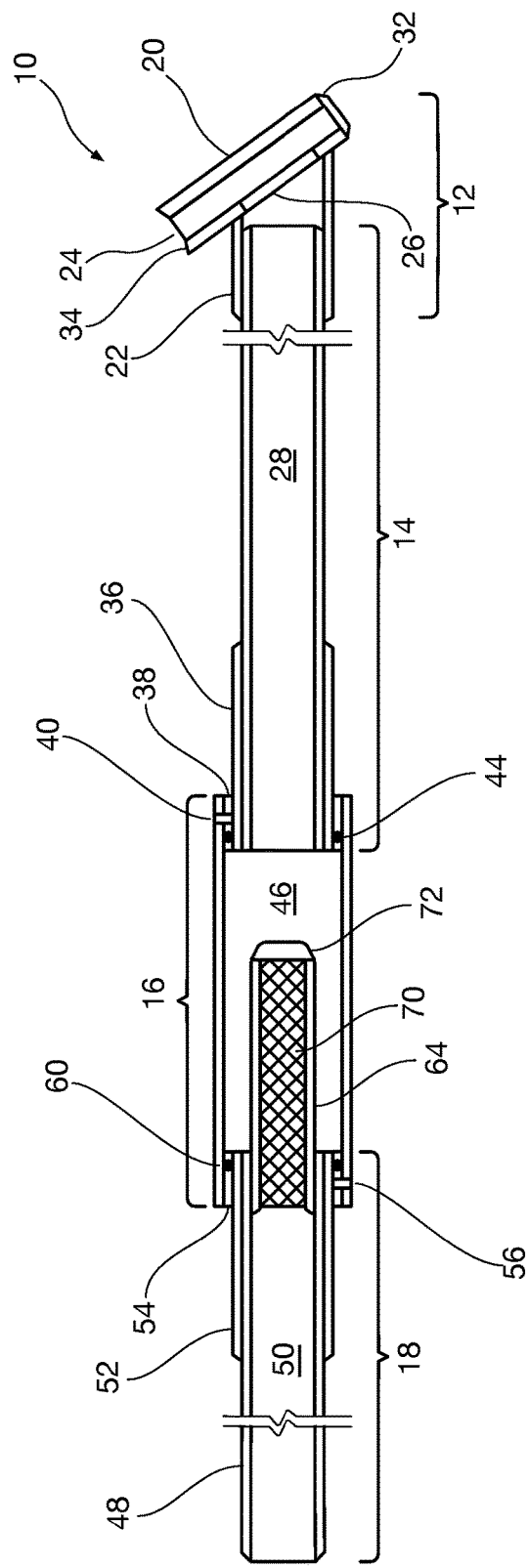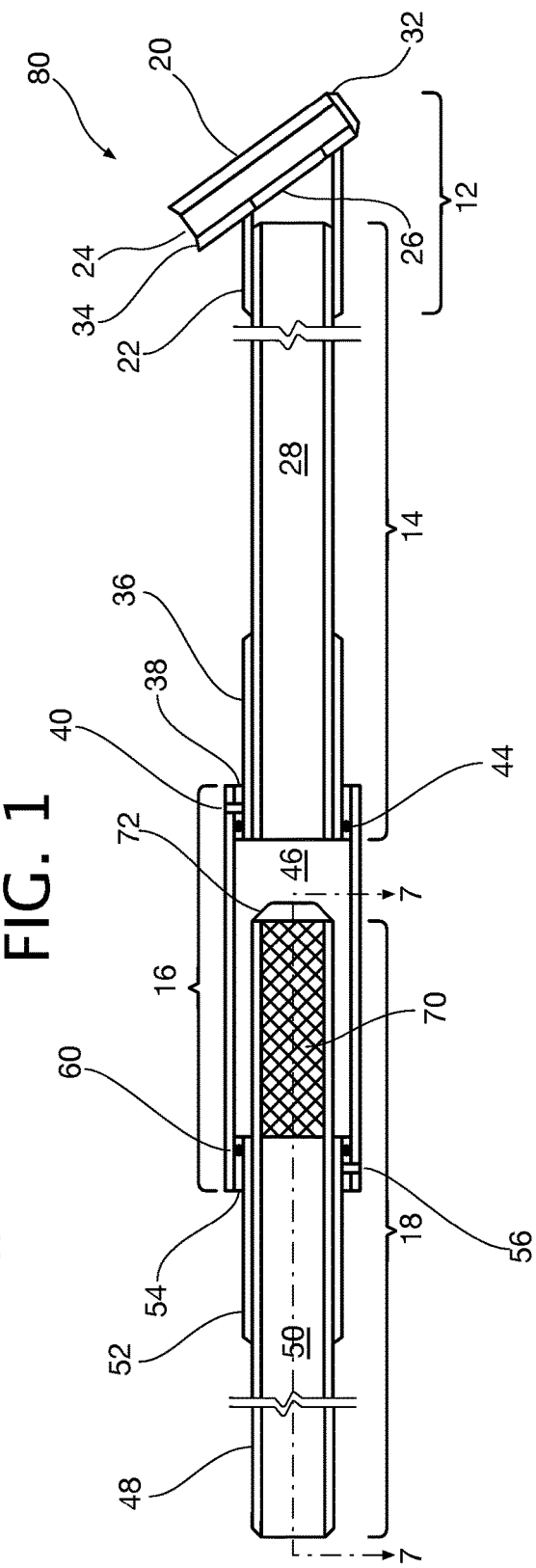

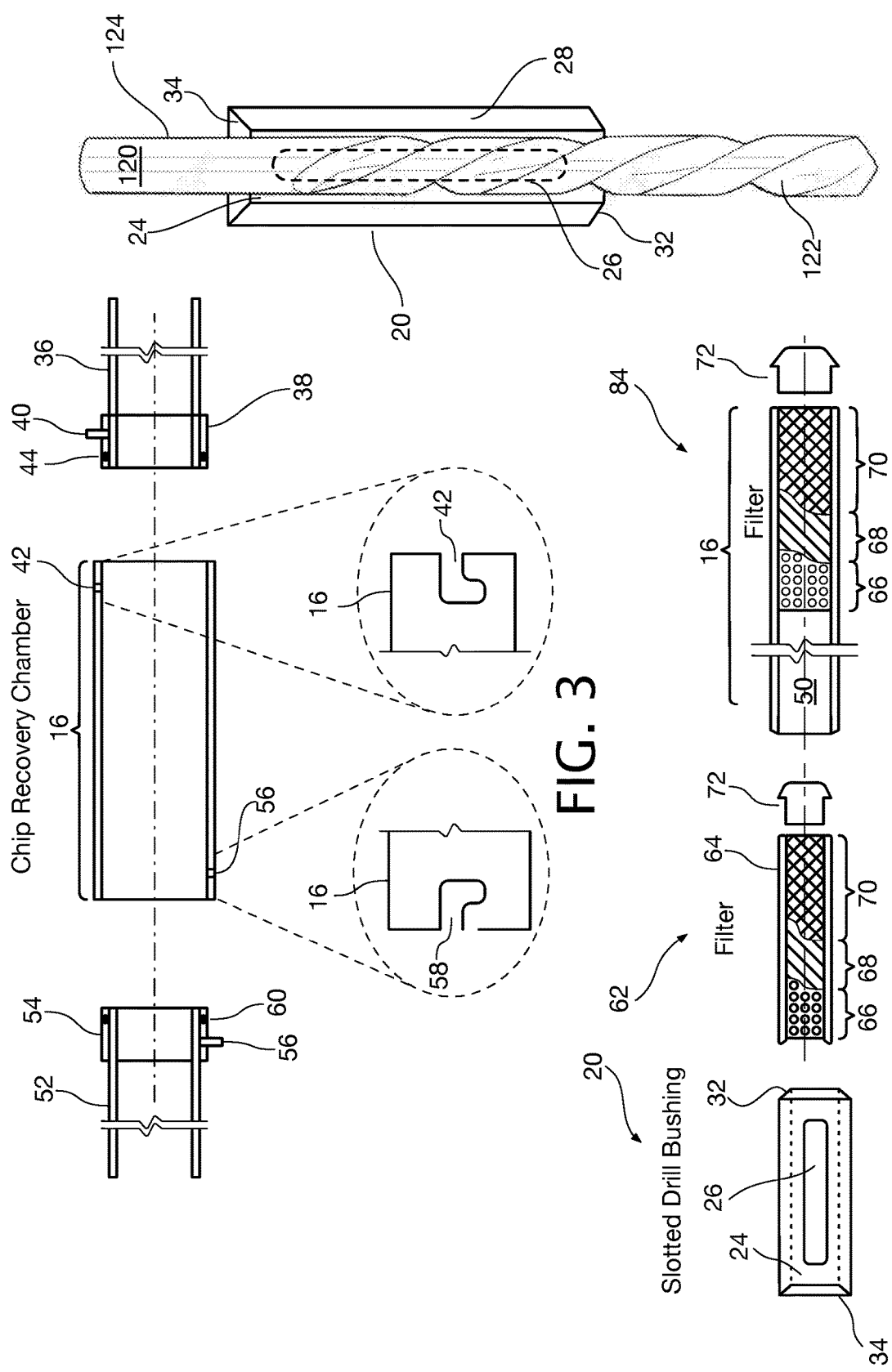

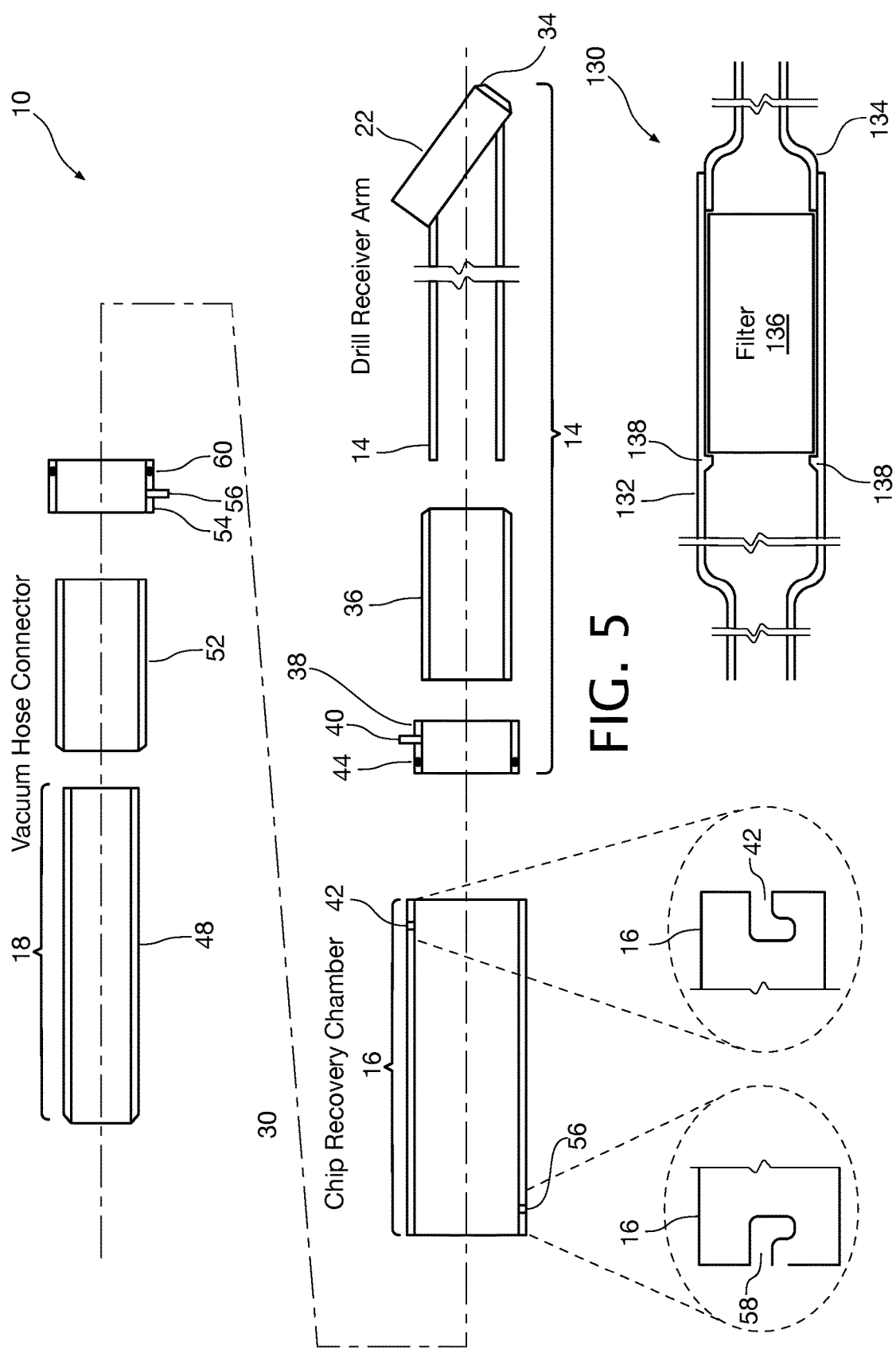

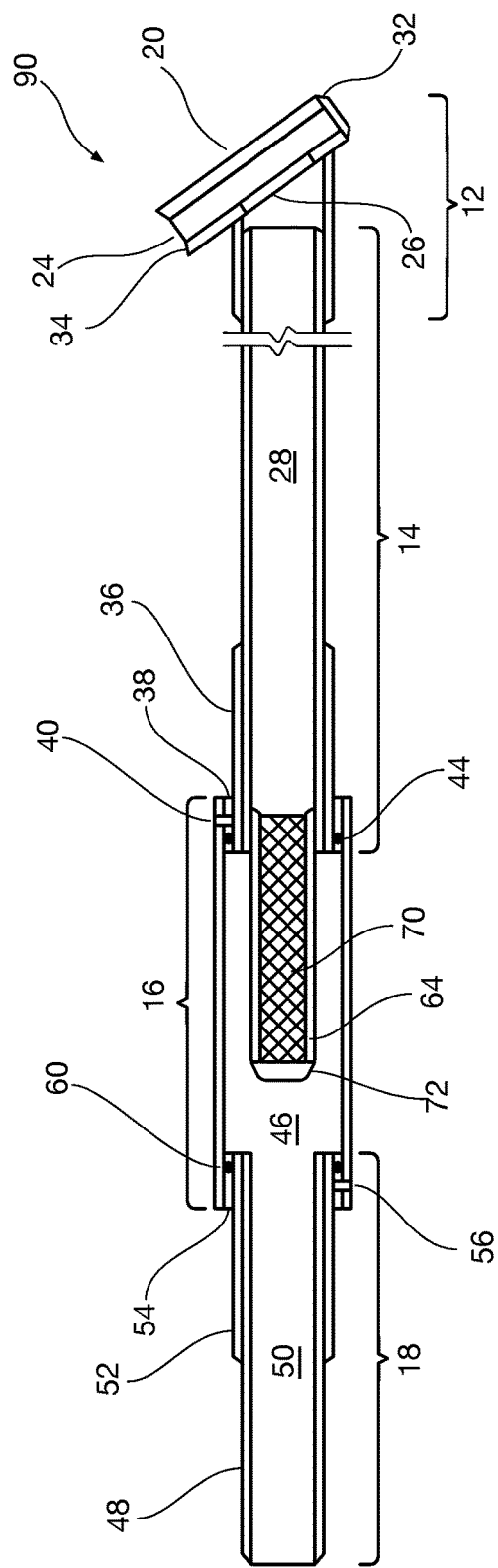
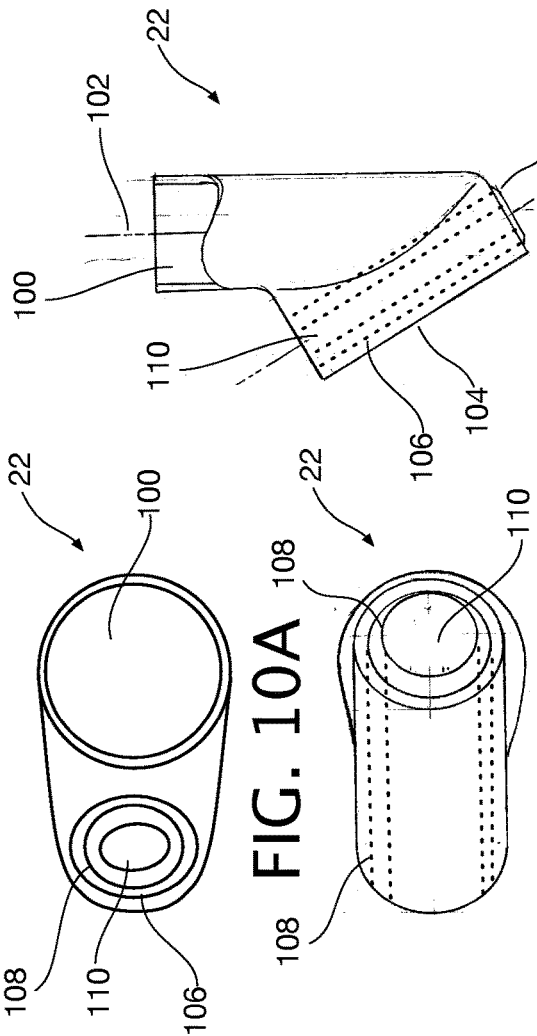
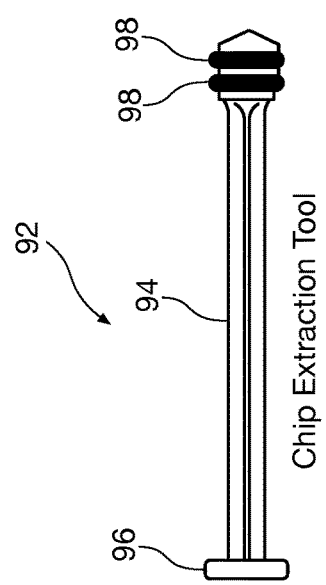
FIG. 8
FIG. 9
FIG. 10A
FIG. 10B
FIG. 10C

VACUUM DRILL GUIDE

FIELD OF THE INVENTION

The present invention relates to surgical instruments. More particularly, the present invention relates to a vacuum drill guide for surgical drills.

BACKGROUND

There are often complications that arise that are associated with drill bits used in performing surgical procedures. Often, these complications include excessive heat build-up, limited accessibility to the surgical site, and removal and containment of bone and bone marrow chip. When a surgeon drills into bone, the cutting edge of the drill bit causes bone and marrow fragment chips to travel up the drill flutes. When the drill flutes become compacted with these chips, the portion of the heat generated by the drilling that is captured by the chips is not removed, and additional heat is generated by frictional contact between the chips and the wall of the hole. In order to overcome this additional friction, drilling torque is increased to maintain the drill speed, further accelerating heat generation. Temperatures in the hole can quickly reach levels that can result in thermo necrosis of the bone tissue.

BRIEF DESCRIPTION

The vacuum drill guide of the present invention was developed in response to complications associated with drill bits used in surgeries. With increased accessibility, the vacuum drill guide of the present invention when used in conjunction with a drill employing a flexible shaft, makes the surgical drilling task easier to complete. The vacuum drill guide allows the drill to continuously clear bone and bone marrow chip, reduces excessive heat, and enables the capture and retrieval of chip bone and bone marrow for harvesting in a containable manner. The vacuum drill guide of the present invention is designed for single use application, eliminating the need for surgical equipment re-sterilization and thereby lessening the chance of infection.

According to an aspect of the invention, a vacuum drill guide includes an elongated structure having an internal axial passageway formed therethrough, a first end of the elongated structure terminating in a drill bushing attached to a first end of the elongated structure, the drill bushing having an axial slot formed in a wall thereof and communicating with the internal axial passageway of the elongated structure, the drill bushing further having a longitudinal bore formed therethrough to receive a drill bit and allow the received drill bit to rotate, a second end of the elongated structure opposite the first end terminating in a vacuum hose fitting communicating with the axial passageway, a chip recovery chamber disposed along the internal axial passageway between the first end and the second end of the elongated structure, and a vacuum filter disposed in the internal axial passageway between the chip recovery chamber and the first end of the elongated structure.

According to an aspect of the invention, the drill bushing is attached to the first end of the elongated structure at an angle of less than 90°.

According to an aspect of the invention, the drill bushing is attached to the first end of the elongated structure by one of friction fitting and an adhesive at the first end of the elongated structure.

According to an aspect of the invention, the longitudinal bore of the drill bushing is integrally formed therethrough to receive a drill bit.

According to an aspect of the invention, the longitudinal bore of the drill bushing is formed in an insert received in a longitudinal aperture in the drill bushing.

According to an aspect of the invention, the elongated structure includes four segments, a first segment including the drill bushing, a second segment including a drill bit receiver arm at the first end of the elongated structure, a third segment including the chip recovery chamber, and a fourth segment including the vacuum hose fitting terminating in the second end of the elongated structure.

According to an aspect of the invention, the first, second, third, and fourth segments are detachable from one another.

According to an aspect of the invention, the vacuum filter is received into an end of the fourth segment opposite an end terminating in the vacuum hose fitting.

According to an aspect of the invention, the, second, third, and fourth segments have diameters selected to allow the second and fourth segments to connect by slip fit into opposite ends of the third segment, and the first segment has a diameter selected to allow the second segment to connect by slip fit into a distal end of the first segment.

According to an aspect of the invention, connecting ends of the second and fourth segments and ends of the third segment include mating fasteners.

According to an aspect of the invention, the mating fasteners are bayonet fittings.

According to an aspect of the invention, the elongated structure is formed from polycarbonate material.

According to an aspect of the invention, the first, second, third, and fourth segments are formed from polycarbonate material.

According to an aspect of the invention, the vacuum filter includes a vacuum filter body, and a layer of filter media disposed over the hollow filter body.

According to an aspect of the invention, the filter media includes a layer of permeable membrane disposed over the hollow filter body.

According to an aspect of the invention, the vacuum drill guide further includes a layer of mesh disposed over the permeable membrane, and an end of the filter body facing the first end of the elongated body is a closed end.

According to an aspect of the invention, the vacuum filter body includes an end of the vacuum hose fitting having radial apertures that is inserted into the chip recovery chamber.

According to an aspect of the invention, the filter body includes an end of the vacuum hose fitting inserted into the chip recovery chamber.

According to an aspect of the invention, a method for operating vacuum drill guide having an elongated structure having an internal axial passageway formed therethrough, the elongated structure, a first end of the elongated structure terminating in a drill bushing attached to a first end of the elongated structure, the drill bushing having an axial slot formed in a wall thereof and communicating with the internal axial passageway of the elongated structure, the drill bushing further having a longitudinal bore formed therethrough to receive a drill bit and allow the received drill bit to rotate, a second end of the elongated structure opposite the first end terminating in a vacuum hose fitting communicating with the axial passageway, a chip recovery chamber disposed along the internal axial passageway between the first end and the second end of the elongated structure, and a vacuum filter disposed in the internal axial passageway between the chip recovery chamber and the first end of the elongated structure, includes providing the vacuum drill guide, inserting a drill bit into the drill bushing, pulling a vacuum from the second end of the elongated structure, and rotating the drill bit to perform a drilling procedure.

According to an aspect of the invention, inserting the drill bit into the drill bushing includes inserting the drill bit into the drill bushing to a depth that exposes at least a portion of flutes on a shaft of the drill bit to the axial slot of the drill bushing.

According to an aspect of the invention, the method further includes ending the drilling procedure, and removing drill waste accumulated in the chip recovery chamber.

According to an aspect of the invention, providing the vacuum drill guide includes providing a vacuum drill guide including four detachable segments, a first segment including the drill bushing, a second segment including the drill receiver arm, a third segment including the chip recovery chamber having a first end attached to the drill receiver arm, the fourth segment including the vacuum hose fitting attached to a second end of the chip recovery chamber, and removing drill waste accumulated in the chip recovery chamber includes detaching the third segment from the second and fourth segments and removing the drill waste from the third segment.

BRIEF DESCRIPTION OF THE DRAWING FIGURES

The invention will be explained in more detail in the following with reference to embodiments and to the drawing in which are shown:

FIG. 1 is a drawing showing a cross-sectional view of an illustrative assembled vacuum drill guide in accordance with an aspect of the present invention;

FIG. 2 is a drawing that is a cross-sectional view of the slotted drill bushing adapted to be attached at the end of the drill bit receiver arm of FIG. 1 turned axially 90° from the view of FIG. 1 to reveal the chip removal slot;

FIG. 3 is a drawing showing a detailed view of the bayonet slots provided at the ends of the chip recovery chamber and used to connect the drill bit receiver arm and the vacuum hose attachment fitting to the chip recovery chamber in accordance with an exemplary embodiment of the present invention;

FIG. 4 is a cross-sectional view of an example of a removable vacuum filter for use in a vacuum drill guide in accordance with the present invention with an end cap removed;

FIG. 5 is an exploded cross-sectional view of the vacuum drill guide of FIG. 1 with the filter removed;

FIG. 6 is a drawing showing a cross-sectional view of an illustrative assembled vacuum drill guide in accordance with an aspect of the present invention;

FIG. 7 is a cross-sectional view of an example of a vacuum filter integrated with the vacuum hose attachment fitting of the vacuum drill guide of FIG. 6 taken along lines 7-7 of FIG. 6 in accordance with the present invention with an end cap removed;

FIG. 8 is a drawing showing a cross-sectional view of an illustrative assembled vacuum drill guide in accordance with an aspect of the present invention;

FIG. 9 is a drawing showing a side view of a chip removal tool that may be employed for conveniently removing the bone and marrow chips from the chip recovery chamber or the bit receiver arm;

FIGS. 10A, 10B, and 10C are three views of a drill bushing assembly that may be used in a vacuum drill guide in accordance with an aspect of the present invention;

FIG. 11 is a drawing that shows a drill bit inserted into the axially aligned bore of the slotted drill bushing to illustrate the positioning of the drill bit with respect to the drill bushing slot; and FIG. 12 is a drawing showing a cross-sectional view of an illustrative assembled vacuum drill guide in accordance with an aspect of the present invention.

DETAILED DESCRIPTION

Persons of ordinary skill in the art will realize that the following description is illustrative only and not in any way limiting. Other embodiments will readily suggest themselves to such skilled persons.

The vacuum drill guide of the present invention provides a means to position and stabilize a drill bit to quickly and accurately form a hole in bone tissue. The vacuum drill guide of the present invention clears bone tissue from the hole and prevents accelerated heat generation due to friction caused by compacted bone chips remaining in the flutes of the drill bit. The vacuum drill guide of the present invention also collects chips of bone tissue as they are removed, maintaining wound cleanliness and securing the bone chips for beneficial use.

Referring first of all to FIG. 1 a cross-sectional view of an exemplary embodiment of a vacuum drill guide 10 in accordance with aspects of the present invention are shown. According to another aspect of the invention, the various components of the vacuum drill guide 10 may be formed using an injection molding process.

The vacuum drill guide 10 includes four sections. A drill bushing assembly 12 is a first section, a drill bit receiver arm 14 is a second section, a chip recovery chamber 16 is a third section, and a vacuum hose attachment fitting 18 is a fourth section.

The drill bushing assembly 12 includes a drill bushing 20 that is disposed on a drill bushing housing 22 that is attached to a distal end of the drill bit receiver arm 14. FIG. 1 shows the end of the drill bushing assembly 12 slip fit over the distal end of the drill bit receiver arm 14 but other attachment mechanisms could be employed. As shown in FIG. 1, the drill bushing assembly 12 may be formed as a separate component and attached to a distal end of the drill bit receiver arm 14 as shown in FIG. 1 or may be joined to and integral with the distal end of the drill bit receiver arm 14 by use of an adhesive or thermal bonding. The drill bushing assembly 12 is preferably formed from a material such as a thermoplastic.

The drill bushing 20 shown in both FIG. 1 and FIG. 2 is a hollow member that has an axially aligned bore 24 formed therethough. The bore 24 is sized to provide a clearance fit for a selected drill bit size with which the vacuum drill guide 10 will be used.

An axially aligned slot 26 is formed in the wall defining the hollow passage of the drill bushing 20 by, for example, milling or injection molding, and communicates with both the axial bore 24 and a passage 28 defined by the inner wall of the drill bushing 20 of the drill bit receiver arm 14 to define an exit path for bone and marrow chip waste removed by a drill bit rotating in the bore 24 of the drill bushing 20 and in contact with bone into which a hole is being drilled. The slot 26 has a width selected to be smaller than the diameter of a drill bit that it will accept.

The drill bushing 20 may have a convex chamfer (indicated by reference numeral 32) formed on the end through which the end of a drill bit will extend and a concave chamfer (indicated by reference numeral 34) formed on the end into which the drill bit will be inserted. The drill bushing 20 is preferably disposed at an angle of less than 90° with respect to the axis of the drill bit receiver arm 14 measured from the end into which the drill bit will be inserted. In one embodiment of the invention the included angle may be about 35°

The drill bit receiver arm 14 is a hollow, preferably cylindrical member having a passage 28 defined by its inner wall and may be formed from a material such as polycarbonate.

A stiffening member 36, which may also be formed from a material such as polycarbonate, may be attached to the proximate end of the drill bit receiver arm 14 to provide additional strength to the vacuum drill guide 10 and to match the diameter of the chip recovery chamber 16.

In one embodiment of the present invention, the drill bit receiver arm 14 is mated to the chip recovery chamber 16 using a bayonet fitting formed from a cylindrical fastening member 38 attached to the drill bit receiver arm 14 and having a pin 40 extending outward in a radial direction. The pin 40 mates with a slot 42 formed in the wall of the chip recovery chamber 16, is pushed into the slot 42 (shown in detail in FIG. 3) and locks into the slot 42 with a twisting motion in a manner known in the art. An O-ring 44 may be disposed in an annular groove formed in the cylindrical fastening member 38 at a location proximate to the end of the cylindrical fastening member 38 that is inserted into the chip recovery chamber 16. The O-ring 44 forms a vacuum seal with an inner wall of the chip recovery chamber 16.

The drill bit receiver arm 14, the stiffening member 36, and the cylindrical fastening member 38 may be fastened together by an adhesive bonding or injection molded as a single piece to form the drill bit receiver arm 14 as a single structure.

The chip recovery chamber 16 is a hollow, preferably cylindrical, member defining a passage 46 and may be formed from a material such as polycarbonate. The chip recovery chamber 16 can also serve as a handle for a surgeon to grasp while using the vacuum drill guide of the present invention.

The vacuum hose attachment fitting 18 is a hollow, preferably cylindrical, member 48 whose inner wall defines a passage 50 and may be formed from a material such as polycarbonate. A stiffening member 52, which may also be formed from a material such as polycarbonate, may be attached to the proximate end of the vacuum hose attachment fitting 18 to provide additional strength to the vacuum drill guide 10 and to match the diameter of the chip recovery chamber 16.

In one embodiment of the present invention, the vacuum hose attachment fitting 18 is mated to the chip recovery chamber 16 using a bayonet fitting formed from a cylindrical fastening member 54 attached to the vacuum hose attachment fitting 18 and having a pin 56 extending outward in a radial direction. The pin 54 mates with a slot 58 (shown in detail in FIG. 3) formed in the wall of the chip recovery chamber 16, is pushed into the slot 58 and locks into the slot 58 with a twisting motion in a manner known in the art. An O-ring 60 may be disposed in an annular groove formed in the cylindrical fastening member 54 at a location proximate to the end of the cylindrical fastening member 54 that is inserted into the chip recovery chamber 16. The O-ring 60 forms a vacuum seal with an inner wall of the chip recovery chamber 16.

Persons of ordinary skill in the art will appreciate that the bayonet fittings employing elements 40, 42, 56, and 58 used to fasten the drill receiver arm 14 and the vacuum hose attachment fitting 18, respectively, to the chip recovery chamber 16 are but one example of fastening structures that may be used for this purpose. Other non-limiting examples of fastening systems that may be used include other twist lock mechanisms, mating threaded ends on the drill bit receiver arm 14, the vacuum hose attachment fitting 18, and the chip recovery chamber 16, and mating friction-fit ends on the drill receiver arm 14, the vacuum hose attachment fitting 16, as well as other suitable fastening means.

The inner diameter of the chip recovery chamber 16 is chosen to form a slip fit with both the cylindrical fastening member 38 of the drill bit receiver arm 14 and the cylindrical fastening member 54 of the vacuum hose attachment fitting 18 and further to provide an adequate volume for the collection of bone and marrow chips pulled by vacuum from flutes of the drill bit through the slot 26 on the drill bushing 20 and through the passage 28 of the drill bit receiver arm 14 and into the chip recovery chamber 16.

The member 48, the stiffening member 52, and the cylindrical fastening member 54 may be fastened together by an adhesive or similar means or may be injection molded to form the vacuum hose attachment fitting 18 as a single structure.

The vacuum drill guide 10 includes a vacuum filter 62 that is slip fit inserted into the passage 46 of the vacuum hose attachment fitting 18. The vacuum filter 62 may be a cylinder formed from a material such as thermoplastic. In the embodiment shown in FIG. 1 the vacuum filter 62 is removable and is slip fit inserted into the passage 46 of the vacuum hose attachment fitting 18.

FIG. 4 is a diagram that shows a partial cutaway view of one illustrative embodiment of a vacuum filter 62. The vacuum filter 62 includes a filter body 64 that may be a cylinder formed from a material such as thermoplastic and is shown including perforations 66 in the form of holes, some of which are shown in the cutaway view of the exemplary embodiment depicted in FIG. 4. A layer of permeable membrane 68 formed from a material such as selectively permeable regenerated cellulose membrane such as dialysis tubing that sold under the trademark Carolina from Carolina Biological Supply Company of Burlington, N.C. and is partially shown in the cutaway view of the exemplary embodiment depicted in FIG. 4. The layer of permeable membrane 68 is covered by a screen material 70 such as a 40-mesh screen formed from a material such as 304 stainless steel, and is partially shown in the cutaway view of the exemplary embodiment depicted in FIG. 4. A cap 72 is fitted into the distal end of the vacuum filter body. Persons of ordinary skill in the art will appreciate that the vacuum filter 62 depicted in FIG. 4 is only a non-limiting example of a vacuum filter that may be used with the vacuum drill guide 10 of the present invention, and that other vacuum filter configurations are contemplated to fall within the scope of the present invention.

Referring now to FIG. 5, an exploded cross-sectional view of the vacuum drill guide of FIG. 1 shows how the components are assembled. The filter is not shown in FIG. 5. The drill bit bushing 22 is shown as being integral with the drill bit receiver arm 14 in accordance with another aspect of the present invention.

Referring now to FIG. 6, a drawing shows a cross-sectional view of an illustrative assembled vacuum drill guide 80 in accordance with an aspect of the present invention. The embodiment of the assembled vacuum drill guide 80 shown in FIG. 6 is similar to the embodiment shown and described with reference to FIG. 1 and the description of the vacuum drill guide 10 of FIG. 1 applies to FIG. 6 with the exception that the body of the vacuum filter is not a separate component but is integrally formed at a proximal end of the vacuum hose attachment fitting 18. The vacuum filter is shown in FIG. 6 with the mesh layer 70 covering the entire length of the filter body.

FIG. 7 is a diagram taken along the lines 7-7 of FIG. 6 that shows a partial cutaway view of one illustrative embodiment of a vacuum filter 84 having a filter body integrally formed at a proximal end of the vacuum hose attachment fitting 18. The proximal end of the vacuum hose attachment fitting 18 that serves as the body of the vacuum filter 84 is shown including perforations 66 in the form of holes, some of which are shown in the cutaway view of the exemplary embodiment depicted in FIG. 7. A layer of permeable membrane 68 formed from a material such as selectively permeable regenerated cellulose membrane such as dialysis tubing that sold under the trademark Carolina from Carolina Biological Supply Company of Burlington, N.C. and is partially shown in the cutaway view of the exemplary embodiment depicted in FIG. 7. The layer of permeable membrane 68 is covered by a screen material 70 such as a 40-mesh screen formed from a material such as 304 stainless steel, and is partially shown in the cutaway view of the exemplary embodiment depicted in FIG. 7. A cap 72 is fitted into the open end of the vacuum hose attachment fitting 18 that serves as the body of the vacuum filter 84. Persons of ordinary skill in the art will appreciate that the vacuum filter 84 depicted in FIG. 7 is only a non-limiting example of a vacuum filter that may be used with the vacuum drill guide 80 of the present invention, and that other vacuum filter configurations are contemplated to fall within the scope of the present invention.

Referring now to FIG. 8, a drawing shows a cross-sectional view of an illustrative assembled vacuum drill guide 90 in accordance with an aspect of the present invention. The embodiment of the assembled vacuum drill guide 90 shown in FIG. 8 is similar to the embodiment shown and described with reference to FIG. 1 and the description of the vacuum drill guide 10 of FIG. 1 applies to FIG. 8 with the exception that the vacuum filter 62 is inserted in the end of the drill bit receiver arm 14 that is inserted into the chip recovery chamber 16. The vacuum filter of FIG. 8 is the same vacuum filter 62 depicted in FIG. 4, and is shown in FIG. 8 with the mesh layer 70 covering the entire length of the filter body. Persons of ordinary skill in the art will appreciate that in the embodiment shown in FIG. 8, the bone and marrow fragment chips that are pulled by vacuum through the vacuum drill guide 10 of the present invention will be trapped inside of the body 64 of vacuum filter 62 rather than on the outside of the outside mesh layer 70 of the vacuum filter 62 in the volume defined by the chip recovery chamber 16.

After the assembled vacuum drill guide 10, 80, or 90 has been used, the bone and marrow fragment chips may be recovered for beneficial use. FIG. 9 is a drawing showing a side view of a chip extraction tool 92 that may be employed for conveniently removing the bone and marrow chips from the chip recovery chamber 16 or the drill bit receiver arm 14, depending on the location and thus the orientation of the vacuum filter as previously described herein. The drill bit receiver arm 14 and the vacuum hose attachment fitting 18 are detached from the chip recovery chamber 16. The vacuum filter is either seated in the passage 28 of the drill bit receiver arm 14, the passage 50 of the vacuum hose attachment fitting 18 or is formed integrally with the end of the vacuum hose attachment fitting 18 depending on which embodiment of the invention is used. The chip extraction tool 92 is then employed to push the bone and marrow chips ahead of it into a container provided by a user.

The chip extraction tool 92 has a shaft 94 with a grasping handle 96 on one end and a pair of O-rings 98 on the other end. The tool is sized so that the O-rings 98 make contact with the inner wall of either the chip recovery chamber 14 or the inner wall of the drill bit receiver arm 12 when it has been detached from the remaining structure.

In order for the vacuum drill guide 10 of the present invention to function properly, the flutes of the drill bit must extend far enough up the shaft of the drill bit such that they communicate with the axially aligned slot 26 in the drill bushing 20. If the portion 124 of the drill bit 120 that extends beyond the ends of the flutes 122 occupies all of the axially aligned slot 26, the bone and marrow fragment chips that are travelling up the drill flutes cannot be removed by the vacuum pulled through the vacuum drill guide 10 of the present invention. When the drill flutes become compacted with these chips, friction is increased, producing heat which can result in thermo necrosis of the bone tissue.

By way of a non-limiting example, in accordance with one embodiment of any of vacuum drill guides 10, 80, and 90 of the present invention, the drill bit receiver arm 14 and the vacuum hose attachment fitting 18 both have outside diameters of 0.375 in., and the chip recovery chamber 16 has an outside diameter of 0.750 in., and the stiffening members 32 and 50 both have outside diameters of 0.50 in. The length of the drill bit receiver arm 14 is 5.25 in., the length of the vacuum hose attachment fitting 18 is 3.50 in., the length of the chip recovery chamber 16 is 3.3 in., the length of the stiffening member 36 is 0.75 in., and the length of the stiffening member 52 is 0.75 in. The wall thicknesses of these elements is 0.0625 in. The lengths of the stiffening members 36 and 52 may be 0.6 inches. Persons of ordinary skill in the art will appreciate that the recited dimensions of the elements of this embodiment are non-limiting examples, are for purposes of illustration only, and do not limit the scope of the invention to an embodiment whose elements have these dimensions.

It has been noted that the drill bit receiver arm 14, the chip recovery chamber 16, the vacuum hose attachment fitting 18, the stiffening members 36 and 52, and the cylindrical fastening members 38 and 54 may be formed from a material such as polycarbonate. Persons of ordinary skill in the art will appreciate that other materials may be used to form these components. The desired properties of such materials are tensile strength of 9,500 psi and modulus of 32K psi. Such skilled persons will appreciate that non-exhaustive examples of such materials include, but are not limited to, polysulfone or acrylic.

Referring now to FIGS. 10A, 10B, and 10C, three views are shown of a drill bushing housing 22 formed as a separate piece that may be used in the vacuum drill guide of the present invention. An advantage of forming the drill bushing housing 22 as a separate piece is that the vacuum drill guide 10 of the present invention can be used with different sized drill bits by attaching a drill bushing housing 22 having the size suited for a particular sized drill bit. In one embodiment of the invention, the drill bushing housing 22 may be formed as a shell 104 that includes an axial cylindrical passage 106 into which different sized bushing inserts 108 can be fitted and bonded into place to accommodate different sized drill bits. FIGS. 10A, 10B, and 10C show a bushing insert with an internal drill bit bore 110 fitted into a cylindrical passage 106. The opening 100 shown in FIG. 10A and FIG. 10C centered along axis 102 is sized to fit either inside or outside of the end of the drill bit receiver arm 14.

In one embodiment of the operation of the invention the flutes of the drill bit communicate with the axially aligned slot 26 in the drill bushing 20 when the drill bit is fully inserted into the drill bushing 20. This aspect of the invention is illustrated in FIG. 11, a drawing showing a cross-sectional view of a drill bushing 20 having a drill bit 120 inserted into its axially aligned bore 24. Flutes of the drill bit 120 are shown at reference numerals 122. The position of the axially aligned slot 26 of the drill bushing 20 which is out of the plane of the drawing is shown in dashed lines identified by the reference numeral 26. As shown in FIG. 11, the portion 124 of the drill bit 120 that extends beyond the ends of the flutes 122 should extend into the upper portion of the slot 26 to allow the vacuum to pull air mostly through the flutes 122 containing the chips, resulting in more efficient cooling of the drill bit. FIG. 11 also shows that the axially aligned slot 26 has a width selected to be smaller than the diameter of the drill bit 120 in order to prevent the drill bit 120 from travelling into the axially aligned slot 26.

Referring now to FIG. 12, a drawing shows a cross-sectional view of an illustrative assembled vacuum drill guide 130 in accordance with an aspect of the present invention. The vacuum drill guide 130 may be fabricated from two injection molded components 132 and 134. The component 132 serves as both the chip recovery chamber 16 and the vacuum hose attachment fitting 18 of the previously-discussed examples. The second component serves as the drill bit receiver arm 14 of the previously-discussed examples. A vacuum filter 136 is inserted into the passage defined by the component 132 and may have a configuration similar to that of the other vacuum filters discussed herein. The vacuum filter 136 is held in place between the edge of component 134 and filter stop projections 138 formed on the inner wall of the component 132. Persons of ordinary skill in the art will appreciate that in the embodiment shown in FIG. 8, the bone and marrow fragment chips that are pulled by vacuum through the vacuum drill guide 130 from the right-hand side of FIG. 12 will be trapped inside the filter 138. 10 of the present invention will be trapped inside of the body 64 of vacuum filter 62 rather than on the outside of the outside mesh layer 70 of the vacuum filter 62 in the volume defined by the chip recovery chamber 16. The filter 136 may be cleaned by removing it after disengaging components 132 and 134.

To use the vacuum drill guide 10 of the present invention, the drill bit receiver arm 14 and the vacuum hose attachment fitting 18 are both inserted and twist locked into place on the chip recovery chamber 16. A vacuum hose (not shown) is fitted on to the exposed distal end of the vacuum hose attachment fitting 16. A drill bit is inserted into the drill bushing 22. A vacuum pump is used to pull a vacuum through the vacuum drill guide 10 and the attached vacuum hose while the surgeon operates the drill. The vacuum pulls the bone and marrow chips from inside the drill bit flutes through the axially aligned slot 26 in the drill bushing 20, through passage 28 in the drill bit receiver arm 14 into the chip recovery chamber 16 where they are trapped by the vacuum filter 62 (or 84) in the embodiment shown in FIG. 1 and FIG. 6. As detailed above, the bone and marrow chips are trapped inside the filter body when the filter 62 is disposed in the drill bit receiver arm 14 and is oriented as shown in FIG. 8.

After the surgeon has finished drilling the number of holes in one or more bones as required by the particular surgical procedure being performed, the drill bit is removed from the slotted drill bushing 20. The drill bit receiver arm 14 and the vacuum hose attachment fitting 18 are both removed from their respective ends of the chip recovery chamber 16. The bone and marrow chips trapped by the filter 62 (or 84) may then be removed and harvested for use, if necessary, in the surgical procedure by employing the removal tool shown in FIG. 9 or by other means. Any of the vacuum drill guides 10, 80, and 90 of the present invention is advantageously disposable and may be discarded at the end of the surgical procedure. This avoids the labor and infection risk that accompanies re-sterilization of surgical instruments in preparation for a subsequent re-use.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A vacuum drill guide comprising:
   an elongated structure having an internal axial passageway formed therethrough;
   a first end of the elongated structure terminating in a drill bushing attached to a first end of the elongated structure, the drill bushing having an axial slot formed in a wall thereof and communicating with the internal axial passageway of the elongated structure, the drill bushing further having a longitudinal bore formed therethrough to receive a drill bit and allow the received drill bit to rotate, a second end of the elongated structure opposite the first end terminating in a vacuum hose fitting communicating with the axial passageway;
   a chip recovery chamber disposed along the internal axial passageway between the first end and the second end of the elongated structure; and
   a vacuum filter disposed in the internal axial passageway between the chip recovery chamber and the first end of the elongated structure.

2. The vacuum drill guide of claim 1 wherein the drill bushing is attached to the first end of the elongated structure at an angle of less than 90°.

3. The vacuum drill guide of claim 1 wherein the drill bushing is attached to the first end of the elongated structure by one of friction fitting and an adhesive at the first end of the elongated structure.

4. The vacuum drill guide of claim 3 wherein the longitudinal bore of the drill bushing is integrally formed therethrough to receive a drill bit.

5. The vacuum drill guide of claim 3 wherein the longitudinal bore of the drill bushing is formed in an insert received in a longitudinal aperture in the drill bushing.

6. The vacuum drill guide of claim 1 wherein the elongated structure comprises four segments, a first segment including the drill bushing, a second segment including a drill bit receiver arm at the first end of the elongated structure, a third segment including the chip recovery chamber, and a fourth segment including the vacuum hose fitting terminating in the second end of the elongated structure.

7. The vacuum drill guide of claim 6 wherein the first, second, third, and fourth segments are detachable from one another.

8. The vacuum drill guide of claim 7 wherein the vacuum filter is received into an end of the fourth segment opposite an end terminating in the vacuum hose fitting.

9. The vacuum drill guide of claim 7 wherein:
the, second, third, and fourth segments have diameters selected to allow the second and fourth segments to connect by slip fit into opposite ends of the third segment; and
the first segment has a diameter selected to allow the second segment to connect by slip fit into a distal end of the first segment.

10. The vacuum drill guide of claim 7 wherein connecting ends of the second and fourth segments and ends of the third segment include mating fasteners.

11. The vacuum drill guide of claim 10 where the mating fasteners are bayonet fittings.

12. The vacuum drill guide of claim 6 wherein the first, second, third, and fourth segments are formed from polycarbonate material.

13. The vacuum drill guide of claim 1 wherein the elongated structure is formed from polycarbonate material.

14. The vacuum drill guide of claim 1 wherein the vacuum filter comprises:
a vacuum filter body; and
a layer of filter media disposed over the hollow filter body.

15. The vacuum drill guide of claim 14 wherein the filter media comprises a layer of permeable membrane disposed over the hollow filter body.

16. The vacuum drill guide of claim 15 further comprising:
a layer of mesh disposed over the permeable membrane; and
wherein an end of the filter body facing the first end of the elongated body being a closed end.

17. The vacuum drill guide of claim 14 wherein the vacuum filter body comprises an end of the vacuum hose fitting having radial apertures that is inserted into the chip recovery chamber.

18. The vacuum drill guide of claim 14 wherein the filter body comprises an end of the vacuum hose fitting inserted into the chip recovery chamber.

* * * * *